(12) United States Patent
Leong et al.

(10) Patent No.: US 7,648,005 B2
(45) Date of Patent: Jan. 19, 2010

(54) CLIP-STYLE HEARING PROTECTOR

(75) Inventors: Waihong Leong, Roswell, GA (US); Scott Madison Belliveau, Plainfield, IL (US); Sean S. Corbin, Morton Grove, IL (US); Ryan Hall, Marlborough, MA (US); Ki Bok Song, Des Plaines, IL (US); James Wolford, Chicago, IL (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 67 days.

(21) Appl. No.: 11/799,264

(22) Filed: Apr. 30, 2007

(65) Prior Publication Data

US 2008/0264429 A1   Oct. 30, 2008

(51) Int. Cl.
*H04R 25/02* (2006.01)
*A61F 11/08* (2006.01)
*A61F 11/12* (2006.01)
*H04R 25/00* (2006.01)
*A61F 11/06* (2006.01)

(52) U.S. Cl. .............. 181/135; 181/130; 381/328; 381/330; 381/381; 128/867

(58) Field of Classification Search ......... 181/135, 181/130, 129, 131; 381/328, 329, 330, 72, 381/23.1, 381, 374, 380; 128/864–867
See application file for complete search history.

(56) References Cited

U.S. PATENT DOCUMENTS

| | | | | |
|---|---|---|---|---|
| 466,725 | A | * | 1/1892 | Miltimore .................. 381/330 |
| 3,667,569 | A | * | 6/1972 | Mackey et al. .............. 181/135 |
| 3,682,268 | A | * | 8/1972 | Gorike ...................... 181/129 |
| 3,915,166 | A |   | 10/1975 | McCrink |
| RE29,487 | E |   | 12/1977 | Gardner, Jr. |
| 4,490,857 | A |   | 1/1985 | Leight et al. |
| 5,420,381 | A |   | 5/1995 | Gardner, Jr. et al. |
| 5,450,496 | A | * | 9/1995 | Burris et al. ............... 381/375 |
| 5,824,966 | A | * | 10/1998 | Leight ...................... 181/130 |

(Continued)

FOREIGN PATENT DOCUMENTS

FR   2 157 177 A5   6/1973

(Continued)

OTHER PUBLICATIONS

"Koss Titanium Earclips with Volume Control," sold by RadioShack® on Internet web page "http://www.radioshack.com/sm-koss-titanium-earclips-with-volume-control-pi-2206192.html" viewed and printed Apr. 6, 2007, pp. 1-2.

(Continued)

*Primary Examiner*—Edgardo San Martin
(74) *Attorney, Agent, or Firm*—Nathan P. Hendon; Denise Stoker

(57) ABSTRACT

A hearing protection device for a human ear. The device has an arm that clips about the pinna. A plug member caps or enters ear canal. The device is biased to provide some force against the plug member so that is stays in position during use. An optional handle may be provided to assist with temporarily pulling the plug member away from the ear canal or providing adjustment. The device may be adapted for use as an ear phone.

16 Claims, 3 Drawing Sheets

U.S. PATENT DOCUMENTS

| | | | |
|---|---|---|---|
| 6,105,714 A * | 8/2000 | Lindgren | 181/135 |
| 6,728,388 B1 | 4/2004 | Nageno et al. | |
| 6,751,331 B2 * | 6/2004 | Eisenbraun | 381/375 |
| 6,785,396 B2 * | 8/2004 | Shirata | 381/381 |
| 6,804,364 B1 * | 10/2004 | De Jonge | 381/381 |
| 6,819,772 B2 | 11/2004 | Amae | |
| 2003/0044038 A1 | 3/2003 | Shirata | |
| 2003/0174853 A1 * | 9/2003 | Howes et al. | 381/370 |
| 2004/0170294 A1 * | 9/2004 | Murozaki et al. | 381/379 |
| 2005/0069145 A1 * | 3/2005 | Sjoqvist | 381/72 |
| 2006/0198544 A1 | 9/2006 | Yueh | |

FOREIGN PATENT DOCUMENTS

| | | |
|---|---|---|
| FR | 2 558 055 A1 | 7/1985 |
| GB | 0 258 280 A | 2/1927 |
| GB | 0 833 506 A | 4/1960 |
| GB | 2 374 684 A | 10/2002 |
| GB | 2 375 967 A | 12/2002 |
| GB | 2 407 513 A | 5/2005 |

OTHER PUBLICATIONS

"Quiet Pro®," Internet web page "http://www.nacre.no/", Nacre®, Trondheim, Norway, viewed and printed Jun. 21, 2007, 1 page.

* cited by examiner

CLIP-STYLE HEARING PROTECTOR

BACKGROUND OF THE INVENTION

High level sound vibrations and perhaps particularly the steady recurring sounds or din in industrial operations are known to cause traumatic hearing impairments and even loss of hearing. Often these types of impairments do not respond to hearing aids or surgery. As would be expected, there are numerous types of hearing protectors for noise deadening or noise reduction.

One type of conventional hearing protection device are foam ear plugs that may be compressed and inserted into the ear, and then allowed to expand to fit the ear canal. While these types of ear plugs may be useful, they can be uncomfortable and difficult to insert correctly. Further, handling the ear plugs to compress, or remove and replace may be unsanitary.

Another type of conventional hearing protection device includes a U-shaped headband having an inwardly directed ear plug affixed to each of the opposed ends. While it is easy and more sanitary to temporarily pull an ear plug away from the ear, the conventional headband may have certain drawbacks and deficiencies. For some persons, ear bands can cause pressure and are very uncomfortable to wear for long periods of time.

For example, the shape of the headband is such that when the ear plugs are mounted in the wearer's ears, portions of the headband may be close to or touching the wearer's head. This can be irritating and uncomfortable to the wearer. In addition, there is no mechanism for adjusting the headband to allow for varying head sizes. A wearer with a large head requires a large distance between the headband ends on which the ear plugs are attached. Unfortunately, as the distance between the headband end increases, so does the tension in the headband. Accordingly, wearers with relatively large heads may experience discomfort due to this high tension in the headband.

In light of the foregoing problems and issues discussed above, it is desired to have a hearing protection device that can comfortably fit a wide variety of users. It is also desired to have a hearing protection device that may be temporarily moved away from the ear without contamination by the hand.

SUMMARY OF THE INVENTION

In one aspect of the present invention, there is provided a clip-on hearing protection device. The device includes a hearing protection device for a single human ear canal, the device including a plug member and an ear clip. The ear clip includes a pressure member having a first end and an opposite second end. The plug member is connected the first end of the pressure member and a bow member is connected to the second end of the pressure member. The bow member is adapted to bias the plug member toward the ear canal.

In another aspect of the present invention, there is provided a clip-on hearing protection device. The device includes a hearing protection device for a single human ear canal, the device including a plug member and an ear clip adapted to wrap about the pinna member of the ear. The ear clip has a pressure means for biasing the plug member toward the ear canal.

In still another aspect of the present invention, there is provided a clip-on hearing protection device for attachment to a single human ear. The device includes an ear clip with a neck member having a first end and an opposite second end, and a flexible, unitary bow member connected to the second end of the neck member. The bow member has a compressible partial helical-spring shape adapted wrap about the pinna of the human ear. A plug member is attached to the first end of the neck member, and a handle is attached to the unitary bow member adjacent the second end of the neck member.

In yet a further aspect of the present invention, there is provided an ear phone device. The device including a plug member and an ear clip. The ear clip includes a pressure member having a first end and an opposite second end. The plug member is connected the first end of the pressure member and a bow member is connected to the second end of the pressure member. A sound transmission device is enclosed within the ear clip for transmitting sound waves through the plug member to the ear canal. The bow member is adapted to bias the plug member toward the ear canal.

Other features of the invention will be in part apparent and in part pointed out hereinafter as well as better understood by practice of the invention. It is to be understood that both the foregoing general description and the following detailed description are exemplary and are intended to provide further explanation of the invention claimed. The accompanying drawings, which are incorporated in and constitute part of this specification, are included to illustrate and provide a further understanding of the clip-on hearing protection device that is the present invention.

BRIEF DESCRIPTION OF THE DRAWINGS

A full an enabling disclosure of the present invention, including the best mode thereof, directed to one of ordinary skill in the art, is set forth more particularly in the remainder of the specification, which makes reference to the appended figures in which.

DETAILED DESCRIPTION OF THE PRESENT INVENTION

Figure 1:
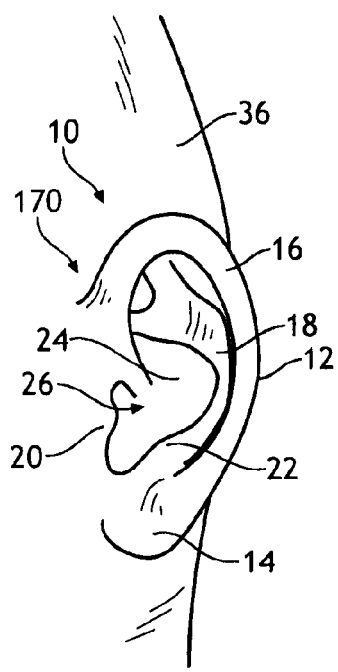
FIG. 1 is a side view of a human ear, illustrated to provide context for the present invention.
Figure 2:
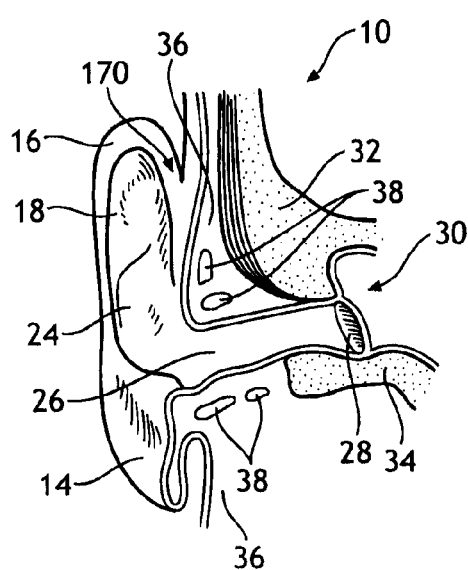
FIG. 2 is a front partial cross-section of a human ear, illustrated to provide context for the present invention.

The present invention is a hearing protector for the human ear 10. In order to provide context for the present invention, a brief discussion of human ear anatomy is presented. Referring to FIG. 1, the externally visible anatomy of the human ear 10 is largely defined by the pinna 12. The pinna 12 has various contours and folds which aid hearing, such as the lobe 14, helix 16, anti-helix 18, tragus 20, and anti-tragus 22. The concha 24 is an indented region roughly defined by the anti-helix 18, tragus 20, and anti-tragus 22. In the concha 24 region, one will find the opening to the ear canal 26. Referring now to FIG. 2, the interior of the ear is shown. In particular, the ear canal 26 is an elongated channel that terminates at the ear drum 28. Beyond the ear drum 28 is a region known as the middle ear 30. The ear drum 28 and the section of ear canal 26 in closest proximity thereto is located between two bony parts of skull, namely the temporal bone 32 and the occipital bone 34. Such bony parts, along with the entire skull, are covered by flesh and adipose material, generically referred to as tissue 36. The pinna 12 is connected to the tissue 36. The pinna 12 stiffness and shape is defined by cartilage 38, seen in cross-section in FIG. 2.

The present invention is a hearing protector 100 that clips to the pinna 12. The hearing protector may be unitary in construction, or assembled from two or more separate parts. Further, the hearing protector 100 will have a left or right orientation, depending on whether it is adaptable for the left or right ear. Regardless of the number of parts or the orientation of hearing protector 100, each embodiment of the present invention has several general sections. For instance, as seen in the embodiment shown in FIGS. 6-7, there is a plug 102 connected to a neck 104. Plug 102 is a pliable member that may conform to a portion of the ear canal 26, or at least the entrance of the ear canal at concha 24. An "ear clip" is defined by a neck 104 that extends from a shoulder 106, and which is connected to an arm 108. Together, the shoulder 106 and arm 108 form a "bow member" that generally extends from the tragus 20, upward to where helix 16 meets tissue 36, and down around the pinna 12 adjacent to where concha 24 meets tissue 36. The arm 108 may further wrap around and contact the lobe 14. The bow member may be biased such that when the hearing protector is clipped to the pinna 12, pressure is applied to the neck 104, forcing the plug 102 toward ear canal 26. Thus, the neck 104 is a "pressure member." Details of the various embodiments of the present invention are described below.

Figure 3:
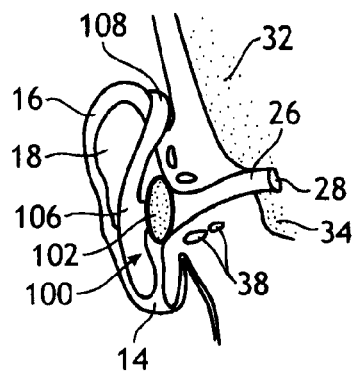
FIG. 3 is the human ear as shown in FIG. 2, with one embodiment of the hearing protector of the present invention disposed on the ear, showing a plug member that covers the ear canal entrance.
Figure 4:
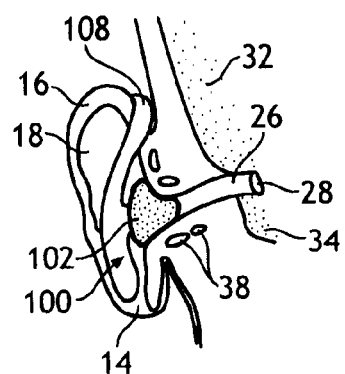
FIG. 4 is the human ear as shown in FIG. 2, with a second embodiment of the hearing protector of the present invention disposed on the ear, showing a plug member that partially enters the ear canal.
Figure 5:
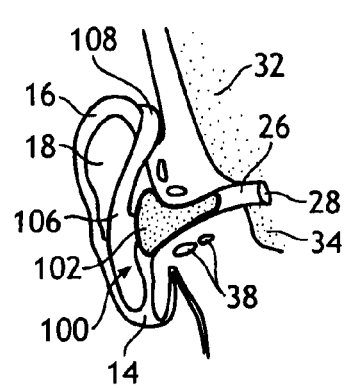
FIG. 5 is the human ear as shown in FIG. 2, with a third embodiment of the hearing protector of the present invention disposed on the ear, showing a plug member that fully enters the ear canal.

Hearing protectors 100 fall generally into three categories, including protectors that covers the entrance to ear canal 26 (referred to as cap devices) (FIG. 3.), protectors which partially enter and seal ear canal 26 between the sections of ear cartilage 38 (referred to as semi-insert devices) (FIG. 4.), and protectors that enter the ear canal and extend further toward the ear drum even with or just past the ear cartilage 38 (referred to as full-insert devices) (FIG. 5).

Hearing protectors 100 which enter the ear canal to a greater degree offer better protection against harmful noise levels because vibrations from the ear cartilage and ear canal tissue is reduced, and the ear canal is at least partially sealed against the noisy environment. However, full-insert and even semi-insert devices may be less comfortable than those which simply cap the ear canal 26. Typically, plugs 102 that cap the ear canal 26 are used for intermittent noise exposures where lighter weight and improved low frequency attenuation are desirable. As used herein, "hearing protectors" refers generally to hearing protectors falling into one of the three categories described above. For reasons of simplicity, the embodiments of the present invention illustrated in FIGS. 6-12 include plugs 102 that operate as cap devices. However, it should be understood that the plugs 102 could be enlarged such that they operate as semi-insert or full-insert devices as shown in FIGS. 4 and 5, respectively.

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

Figure 6:
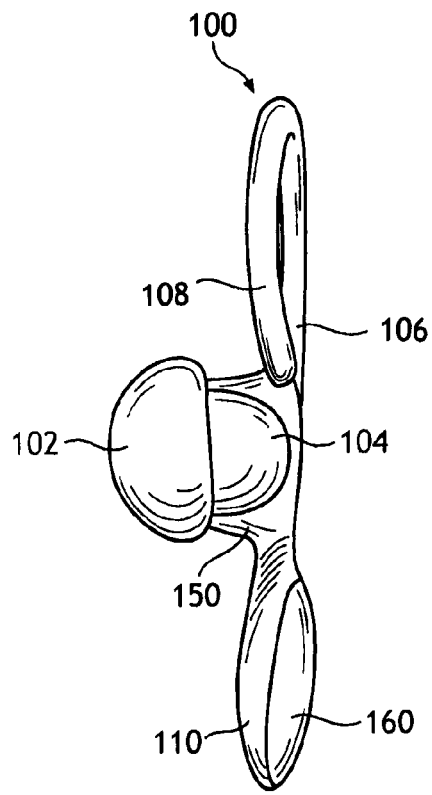
FIG. 6 is a front elevation view of a fourth embodiment of the hearing protector of the present invention, shown in a biased state.
Figure 7:
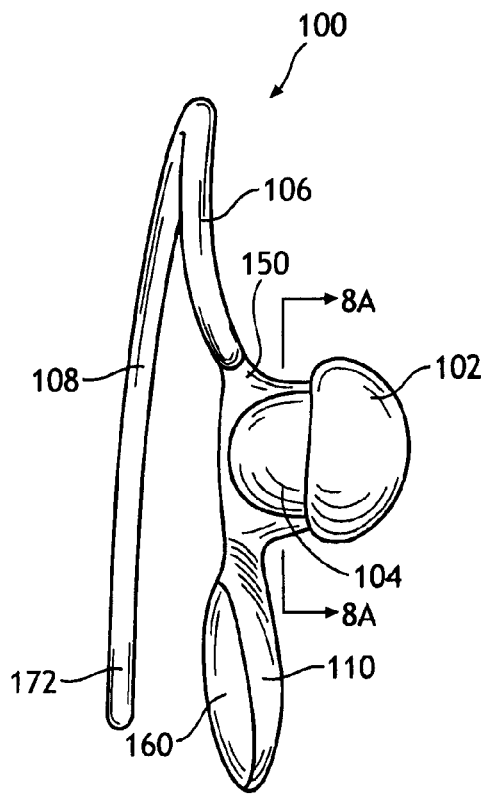
FIG. 7 is a front elevation view of the hearing protector of FIG. 6, shown in an unbiased state.

As shown in FIGS. 6-7, a first embodiment of hearing protector 100 desirably has a unitary construction, with the possible exception of the plug 102. The neck 104, shoulder 106, handle 110, and arm 108 may be molded from a plastic material having the following characteristics: flexible enough to move the arm 108 to the backside of pinna 12 as neck 104 is positioned near the concha 26; durable enough to be used more than one time; moldable, as by injection molding or the like; and steady-state in that it does not exhibit significant loss of stiffness under a continuous load, allowing neck 104 and plug 102 to maintain an effective force toward the ear canal 26. Desirably, a material such as polyethylene is used. However, it is contemplated that the ear clip portion of hearing protector 100 may be manufactured from nylon, plastics such as polypropylene, polyvinyl chloride, polycarbonate; metals such as titanium, steel, or aluminum composites; or elastomer such as silicon, thermoplastic elastomer (TPE), polyurethane rubber, ethylene propylene rubber, or a combination thereof.

Referring to FIG. 7, a plug 102 is connected to the neck 104. The ear plug 102 may be a separate button of a flexible material as described below, shaped so that it is sufficiently seats against the concha 26, tragus 20 and anti-tragus 22 surrounding the entrance to the ear canal 26. Plug 102, when functioning as a cap (FIG. 3) may be of a generally hemispherical shape and has a diameter somewhat greater than that of the average adult human ear canal, or another rounded shape.

For semi-insert or full-insert plugs (FIGS. 4-5), the plug 102 of the invention may be substantially cylindrical in shape and have a diameter somewhat greater than that of the average adult human ear canal. For instance, a diameter of between about 7 cm and about 15 cm is generally acceptable. Desirably, the diameter of the earplug will be between 8 cm and 14 cm. Further, it should be noted and understood that the term "cylindrical" as employed herein includes within its scope structures having a relatively shallow truncated cone shape or a substantially spherical shape. Where the earplug takes the form of a truncated cone, the above diameter criteria may be taken at the midpoint of the cone. Where the earplug is spherical, the above criteria may be applied to the diameter of said sphere.

Plug 102 may be connected to neck 104 in a variety of ways. A first exemplary embodiment of a plug-neck connection, shown in FIG. 8B, has a stem 120 that is placed a corresponding cavity 122 in plug 102. This type of arrangement may allow the wearer to change only the plug 102, and reuse the remaining portion of the hearing protector 100. If the stem 120 is long enough to fit at least partially into the ear canal 26 (FIG. 4 or 5), the stem 104 is preferably flexible so that it flexes as the wearer adjusts the hearing protective device. A non-pliable stem may cause discomfort as the wearer adjusts the hearing protection device. To provide a secure fit in the cavity 122, the stem 120 may be made from a compressible, resilient material and have a width dimension slightly larger than the width dimension of cavity 122; when the stem 120 is positioned in cavity 122, the stem 104 will press against the wall defining cavity 122 to provide a friction fit. It is further contemplated that a more permanent connection between stem 120 and plug 102 may be achieved with an adhesive. Adhesives such as hot-melt glue, cyanoacrylate glue, casein glue, cement glue, resin glue would be suitable for this purpose.

Figure 8A:
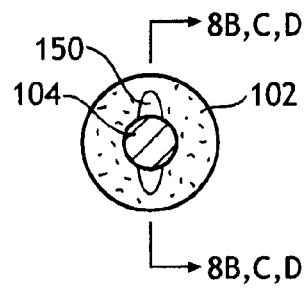
FIG. 8A is a partial cross section of the hearing protector of FIG. 7, taken at the plane defined by line 8A-8A.
Figure 8B:
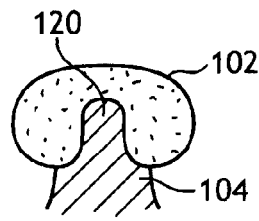
FIG. 8B is a partial cross-section of the hearing protector of FIG. 8A, showing one embodiment of the plug member attachment to the stem, and taken at the plane defined by line 8BCD-8BCD.
Figure 8C:
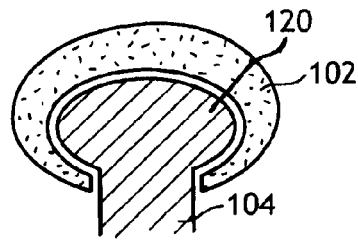
FIG. 8C is a partial cross-section of the hearing protector of FIG. 8A, showing one embodiment of the plug member attachment to the stem, and taken at the plane defined by line 8BCD-8BCD.

In a second exemplary embodiment of a plug-neck connection, shown in FIG. 8C, the neck 104 has a mushroom-shaped stem 130. A plug 102 having a corresponding mushroom-shaped cavity 132 therein is disposed over stem 130. Desirably, there is enough tension in the annulus 134 at the entrance of the cavity 132 to keep the plug 102 from slipping off of the stem 130 as the hearing protector is adjusted within or removed from the ear.

Figure 8D:
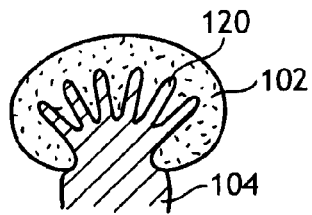
FIG. 8D is a partial cross-section of the hearing protector of FIG. 8A, showing one embodiment of the plug member attachment to the stem, and taken at the plane defined by line 8BCD-8BCD.

In a third exemplary embodiment of a plug-neck connection, shown in FIG. 8D, the neck 104 has a flanged end 140. A plug 102 is adhesively connected to the flanged end 140 by an adhesive as previously described for the stem of FIG. 8B and/or a mechanical connection.

It is to be understood that the particular compound for making plug 102 is less important than the mechanical qualities of the plug 102. Most desirably, the earplug, when deformed, will tend to recover its original shape and size. The conformity of the foamed polymeric composition will create a seal against the ear wall to block sound from entering into ear canal. The principal characteristics exhibited by the ear plug materials are that it is soft and pliable to conform to the shape of the ear canal and ear canal entrance.

In one embodiment, the plug 102 material may have a skin formed on its outer surface, with the skin broken to permit the venting of the ear canal (not shown). With the open-cell construction of the plug 102, air may slowly escape from the ear canal to the surrounding atmosphere until the pressures are equalized. If the atmospheric pressure increases, the pressure within the ear canal may again be equalized to eliminate dizziness, vertigo, or other discomfort. It will be realized that the rate of flow of air through the open cell foam will be relatively slow and hence, the pressure equalization will not in any way affect the sound attenuating properties of the hearing protector 100.

In each of the exemplary embodiments described herein, the plug 102 may be made from dynamically stiff foam. One suitable dynamically stiff foam is described in U.S. Pat. No. 5,420,381, the contents of which are incorporated herein by reference to the extent they are consistent with the present invention. Alternatively, the plug 102 may comprise any other conventional earplug foam material such as the foam disclosed in U.S. Reissue Pat. No. 29,487, all of the contents of which are also incorporated herein by reference to the extent it is consistent with the present invention. In yet another embodiment, plug 102 may be made from silicon rubber. However, it is noted that any flexible polymeric material which can be foamed so as to result in a formed plug structure meeting the design criteria set forth herein constitutes a satisfactory material of construction in the plugs 102 of the invention. Accordingly, polymers of ethylene, propylene, vinyl chloride, vinyl acetate, diisocyanate, cellulose acetate or isobutylene can all be generally employed.

The neck 104 may have a solid cross-section as seen in FIG. 8A. Desirably, neck 104 is substantially cylindrical in shape, but may have other shapes that fit into the concha 24, between the tragus 20 and anti-tragus 22. A flange 150 may provide strength to the junction between the shoulder 106 or handle 110 and the neck 104. However, the precise shape of the neck and flange may be greatly influenced by aesthetic design, and it is contemplated that other shapes would be suitable, as evidenced by the other embodiments of hearing protector 100 described herein.

Shoulder 106 is a section of the hearing protector 100 that will experience relatively high stress as compared to the neck 104 and the arm 108. Shoulder 106, operates as the spring member of hearing protector 100. With respect to a reference plane that lies along line 8A-8A of FIG. 7, and 8BCD-8BCD of FIG. 8A, shoulder 106 operates to project arm 108 away from the reference plane. When the hearing protector 100 is clipped about the pinna 12, the arm 108 is forced in a direction toward the reference plane. In this regard, the shoulder 106 operates as a partial helical spring. The shoulder 106 is then under stress, and it too, may flex closer toward the reference plane. The hearing protector 100 appears more flattened which in use, and is in a stressed state (see FIG. 6). Shoulder 106 may have a curved appearance when viewed from the side, similar to the embodiment shown in FIG. 12. However, it is contemplated various other curvatures or aesthetic shapes may be incorporated into the shoulder 106 shape without affecting functionality.

Handle 110 is an optional feature that enables a user to conveniently grip the hearing protector 100 to spread the bow member for attachment to the ear. Handle 100 may also be used to temporarily pull the plug 102 away from the ear canal 26 or adjust the position of plug 102. Handle 110 is generally an elongated shape. However, as it is only used as a handle and may not experience as much stress as other sections of hearing protector 100, handle 110 may incorporate many aesthetic features without affecting its function. For example, a separate material 160 may be overlaid onto or otherwise attached to handle 110 to add visual interest and/or a different tactile feature. It is contemplated that handle 110 may be constructed from a unitary member.

Arm 108 is a flexible member that curves about pinna 12 from about junction 170 (where the helix 16 meets the head tissue 36) to the back of the pinna (see FIGS. 1 and 2).

Desirably, the distal end 172 (FIG. 7) may hang down near the lobe 14, or even partially wrap around the concha 24. This configuration makes it easier to remove and replace the hearing protector 100 onto the ear. Also desirably, the distal end is rounded so as to increase comfort.

As mentioned previously, the neck 104, shoulder 106, and arm 108 may be constructed as a unitary piece, as by injection molding. However, it is contemplated that these regions could include one or more parts or over-molded pieces, similar to the embodiments of FIGS. 9-12, as discussed herein.

In operation, the device of FIGS. 6-7 is biased toward the ear so that the neck 104 will press the plug 102 inward toward a position capping the ear canal 26. To apply the hearing protector of FIG. 7, the arm 108 is placed behind the pinna 12 so that is rests against a portion of pinna 12 such as the concha 24, and the head tissue 36. The wearer disposes the plug 102 into or over the entrance of the ear canal 26. When the hearing protector is applied in this manner, it appears more flattened, as in FIG. 6. The neck 104 and plug 102, by bearing against the portion of the ear surrounding the entrance to the canal, reduces the amount of sound that is transmitted along the canal and also reduces the sound transmitted by the flesh and bone structure to the middle and inner ear. The hearing protector 100 shown FIG. 3, while aesthetically different, operates in the same manner.

Figure 9:
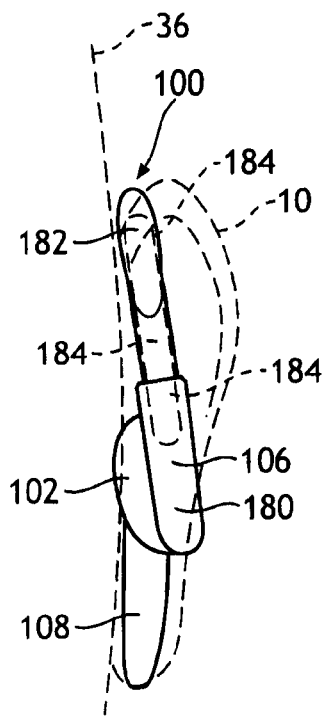
FIG. 9 is a front elevation view of a fifth embodiment of the hearing protector of the present invention, shown in a biased state as it engages an ear.
Figure 10:
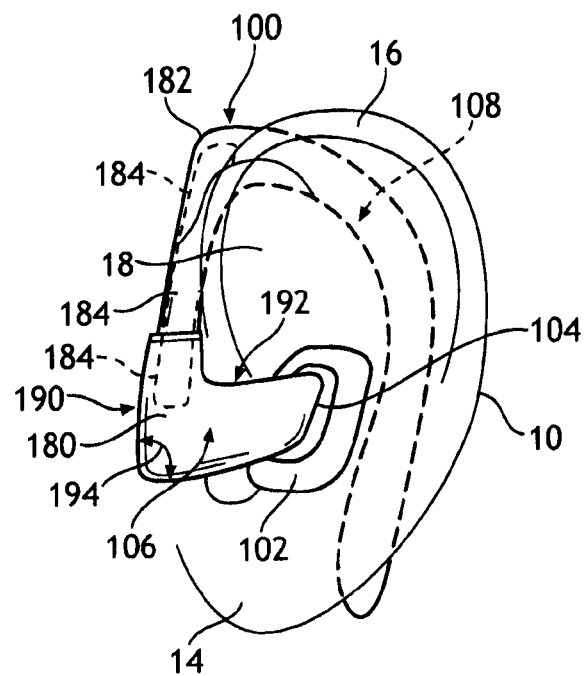
FIG. 10 is a side elevation view of the hearing protector of FIG. 9.

A second exemplary embodiment of the hearing protector 100, shown in FIGS. 9-10, is assembled from several separate parts. Generally, the hearing protector 100 of this embodiment operates the same way, but provides more opportunity for aesthetic enhancement and for optimizing strength properties in particular regions of hearing protector 100, such as the shoulder 106. This may provide opportunity to provide a higher performance hearing protector 100 at a lower cost. As may be seen, the overall shape of the hearing protector is more angular. This may be purely aesthetic, or be due to the use of a straight component, as described herein.

In this particular embodiment, a first component is the neck 104 and a portion of the shoulder 106, which collectively define an elbow 180. A second component is a spring 184, which is a member that functions as a torsion spring. A third component is the arm 108 and integrally-connected partial-sleeve 182. Sleeve 182 overlaps a portion of the shoulder region 106 where it connects to spring 184. Yet a fourth component is the plug 102, that attaches to the neck in the way described in the previous embodiment.

The neck 104 and shoulder 106 may be constructed from a molded plastic such as polyethylene, polypropylene, polyvinyl chloride, polycarbonate, and the like. Arm 108, along with integral sleeve 182, is desirably a flexible member manufactured from the same type of materials described for the embodiment shown in FIG. 6. The spring 184 may be constructed from various metals or composite materials, for example, spring steel.

Desirably, elbow 180 is an L-shaped member having a short leg 190 and a long leg 192. Short leg 190 and long leg 192 may merge at approximately an angle 194 ranging from about 85 to 90 degrees. The short leg 190 includes a straight section for receiving the spring 184. The long leg 192 may be straight as shown, or more curved.

As compared to the neck 104 and corresponding plug 102 of the previous embodiment (FIG. 6), the neck 104 and plug 102 may have a rectangular or other angular shape that fits between the tragus 20 and anti-tragus 22 to cover the ear canal 26. However, it is contemplated that the neck 104 of this particular embodiment may be round, oval, or any shape that functions to adequately cover the ear canal 26.

Torsion spring 184 may be permanently attached to the elbow 180 and sleeve 182 with an adhesive such as cyanoacrylate glue, casein glue, cement glues, resin glues. In the alternative, such connections may be made with an interference fit between the members.

Referring still to FIG. 10, in another embodiment of the present invention, the hearing protector 100 may differ from the previous embodiment by attaching the spring 184 to elbow 180 with a rotating connection. While the rotating connection may allow the elbow 180 to freely rotate with respect to spring 184, it is desirable that an increased resistance to rotation is experienced when the plug 102 is placed in or against the ear canal. This is to maintain adequate pressure against between the plug 102 and ear canal 26 opening, and thus, prevent plug 102 from falling away from the ear canal during use. The increased resistance may be achieved by a detent located between the spring 184 and the elbow 180. In the alternative, the increased resistance may be achieved other ways, such as by a screw thread. Regardless of the exact structure used to create increased resistance, it will likely be caused by material interference between the spring 184 and elbow 180. It is further contemplated that the spring 184 in this particular embodiment may be stiff enough to be ineffective as an actual spring.

Referring still to FIG. 10, in yet another embodiment of the present invention, the hearing protector 100 may be constructed from a flexible, semi-rigid unitary member (similar to the embodiment of FIG. 6) that is reinforced and/or aesthetically enhanced with additional components. In this embodiment, the shoulder region 106 is partly defined by an elbow member 180. The elbow member may merely be a cover constructed from a plastic or rubber type material, and may be the same in appearance or feel, or may be different. Likewise, sleeve member 182 used to cover the arm 108, and may extend to partially cover the shoulder 106 as shown. The sleeve member may be a cover constructed from a plastic or rubber type material, which may be the same in appearance or feel, or may be different. The section of shoulder 106 located between elbow member 180 and sleeve 182 may be relatively straight for aesthetic reasons.

Figure 11:
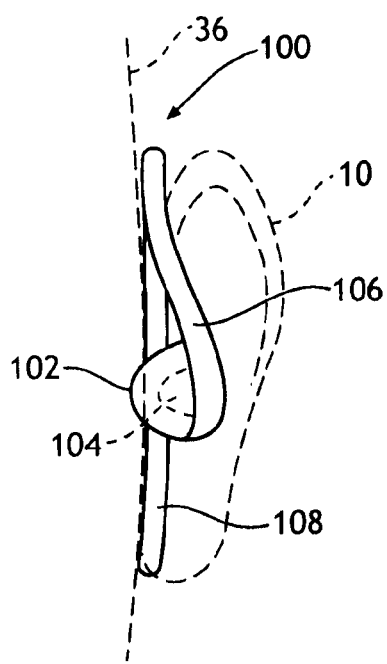
FIG. 11 is a front elevation view of a fifth embodiment of the hearing protector of the present invention, shown in a biased state as it engages an ear.
Figure 12:
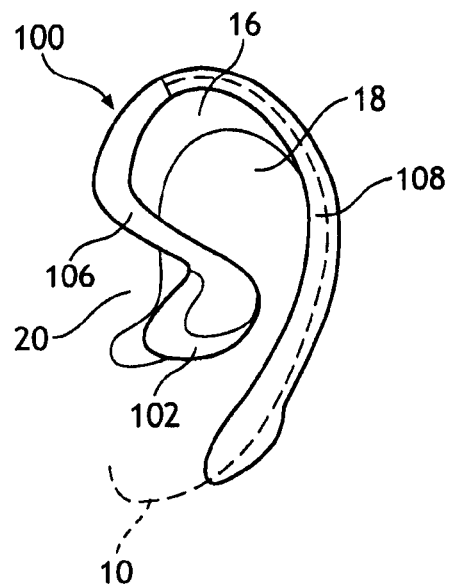
FIG. 12 is a side elevation view of the hearing protector of FIG. 11.

In another exemplary embodiment of the present invention, shown in FIGS. 11 and 12, hearing protector 100 may be of unitary construction, or may be constructed from three separate components. Desirably, the three components include a plug 102/neck 104; a shoulder 106; and an arm 108. In this embodiment, the plug 102 may like that described for the previous embodiments. The neck 104 may be integrally connected to the shoulder 106, which are formed from a rigid plastic such as polyethylene, polypropylene, polyvinyl chloride, and polycarbonate. Desirably, the arm 108 is attached to an end of the shoulder 106 opposite the neck 104.

Arm 108 may be the flexible plastic material as described for the embodiment of FIG. 6. Desirably, arm 108 is a relatively soft, pliable rubber-like material that is reinforced with an embedded stiffening wire. Arm 108 is joined to the end of shoulder 106 by an adhesive such as cyanoacrylate glue, casein glue, cement glues, resin glues. The stiffening wire is partially embedded into shoulder 106 for additional strength at this joint.

Although only a few exemplary embodiments of this invention have been described in detail above, those skilled in the art will readily appreciate that many modifications are possible in the exemplary embodiments without materially departing from the novel teachings and advantages of this invention. For example, any of the embodiments of the present invention may be adapted for use as an ear phone (not shown). As one skilled in the art of ear phone technology will realize, electronics for transmitting sound may be embedded in the ear clip and attached to speaker located in the neck 104. The plug member 102 may at least partially cover the speaker.

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

The invention claimed is:

1. A hearing protection device for a single human ear canal, the device comprising:
   a plug member; and
   an ear clip comprising:
      a pressure member comprising a first end and an opposite second end, wherein the plug member is connected to the first end of the pressure member; and a bow member connected to the second end of the pressure member;

wherein the bow member comprises a partial helical spring that is adapted to bias the plug member toward the ear canal.

2. The hearing protection device of claim 1 wherein the plug member is defined by a cap member.

3. The hearing protection device of claim 1 wherein the plug member is defined by a semi-inserted plug member.

4. The hearing protection device of claim 1 wherein the plug member is defined by a fully-inserted plug member.

5. The hearing protection device of claim 1 wherein the bow member comprises a pliable arm.

6. The hearing protection device of claim 5 wherein the pliable arm is reinforced with a stiffening member.

7. The hearing protection device of claim 6 wherein the pressure member comprises a stem protruding from the first end, wherein the plug member is attached to the stem.

8. The hearing protection device of claim 1 wherein the bow member comprises a shoulder member attached to an arm member.

9. The hearing protection device of claim 8 wherein the shoulder member and arm member are integrally connected.

10. The hearing protection device of claim 1 further comprising a handle extending from the pressure member.

11. A hearing protection device for a single human ear canal, the device comprising:

a plug member; and an ear clip adapted to wrap about a pinna member of the ear, the ear clip comprising a pressure means for biasing the plug member toward the ear canal, wherein the pressure means comprises a torsion spring.

12. The hearing protection device of claim 11 wherein the plug member is defined by a cap member.

13. The hearing protection device of claim 11 wherein the plug member is defined by a semi-inserted plug member.

14. The hearing protection device of claim 11 wherein the plug member is defined by a fully-inserted plug member.

15. A hearing protection device for attachment to a single human ear, the device comprising:

an ear clip comprising a neck member having a first end and an opposite second end, and a flexible, unitary bow member connected to the second end of the neck member wherein the bow member comprises a compressible partial helical-spring shape adapted wrap about the pinna of the human ear;

a plug member that is attached to the first end of the neck member and adapted to cap the ear canal; and a handle attached to the unitary bow member adjacent the second end of the neck member.

16. An earphone for a single human ear canal, the device comprising:

a plug member; and an ear clip comprising:

a pressure member comprising a first end and an opposite second end, wherein the plug member is connected to the first end of the pressure member;

a bow member connected to the second end of the pressure member; and a sound transmission device enclosed within the ear clip for transmitting sound waves through the plug member to the ear canal;

wherein the bow member comprises a partial helical spring that biases the plug member toward the ear canal.

* * * * *